United States Patent [19]

Seelmann-Eggebert et al.

[11] Patent Number: 4,914,172

[45] Date of Patent: * Apr. 3, 1990

[54] WATER-SOLUBLE COPOLYMERS AND THEIR PREPARATION

[75] Inventors: Hans-Peter Seelmann-Eggebert, Schriesheim; Dieter Boeckh; Heinrich Hartmann, both of Limburgerhof; Wolfgang Trieselt, Ludwigshafen, all of Fed. Rep. of Germany

[73] Assignee: BASF Aktiengesellschaft, Ludwigshafen, Fed. Rep. of Germany

[ * ] Notice: The portion of the term of this patent subsequent to Jan. 30, 2007 has been disclaimed.

[21] Appl. No.: 179,477

[22] Filed: Apr. 8, 1988

[30] Foreign Application Priority Data

Apr. 11, 1987 [DE] Fed. Rep. of Germany ....... 3712317
Mar. 4, 1988 [DE] Fed. Rep. of Germany ....... 3807086

[51] Int. Cl.$^4$ ..................... C08F 210/02; C08F 30/04
[52] U.S. Cl. .................... 526/318.3; 526/240
[58] Field of Search ........................ 526/318.3, 240

[56] References Cited

U.S. PATENT DOCUMENTS

| | | | |
|---|---|---|---|
| 2,884,336 | 4/1959 | Loshack et al. | 526/240 |
| 3,137,660 | 6/1964 | Jones | 526/238.2 |
| 3,769,254 | 10/1973 | Anderson et al. | 526/87 |
| 4,267,103 | 5/1981 | Cohen | 526/208 |

*Primary Examiner*—Joseph L. Schofer
*Assistant Examiner*—N. Sarofim
*Attorney, Agent, or Firm*—William G. Conger; Joseph D. Michaels

[57] ABSTRACT

Water-soluble copolymers having a K value of from 8 to 100 (determined according to H. Fikentscher on sodium salt in aqueous solution at 25° C., a pH of 7 and a polymer concentration of the Na salt of 1% by weight) contain, in polymerized form, (a) not less than 15 mol % of one or more monoethylenically unsaturated $C_3$-$C_6$-monocarboxylic acids,
(b) from 0.5 to 84.5 mol % of one or more ethylenically unsaturated $C_4$-$C_6$-dicarboxylic acids,
(c) from 0 to 20 mol % of one or more hydroxyalkyl esters, where hydroxyalkyl is of 2 to 6 carbon atoms, of monoethylenically unsaturated $C_3$-$C_6$-carboxylic acids,
(d) from 0 to 30 mol % of other water-soluble, monoethylenically unsaturated monomers copolymerizable with (a), (b) and (c),
(e) from 0.5 to 15 mol % of a comonomer which possesses two or more ethylenically unsaturated, nonconjugated double bonds and one or more —CO—OH groups and/or their salt with an alkali metal, ammonium or alkaline earth metal base and, if required,
(f) up to 10 mol % of one or more comonomers which differ from (e) and possess two or more ethylenically unsaturated, nonconjugated double bonds, are prepared by copolymerization of the monomers (a) to (f) and are used for coating seed.

5 Claims, No Drawings

WATER-SOLUBLE COPOLYMERS AND THEIR PREPARATION

WO Application 85/01736 discloses that seed can be coated with a polymer mixture which is hygroscopic. The mixture consists of finely divided crosslinked polyacrylamides and finely divided crosslinked polyacrylates. These mixtures may contain graphite. The seed coated therewith germinates more rapidly than untreated seed. However, the disadvantage is that the high molecular weight, crosslinked polymers are virtually completely non-biodegradable.

It is an object of the present invention to provide substantially biologically degradable coating agents for seed.

We have found that this object is achieved, according to the invention, by water-soluble copolymers based on monoethylenically unsaturated carboxylic acids of 3 to 6 carbon atoms, if the copolymers have a K value of from 8 to 100, preferably from 20 to 80 (determined on the sodium salt according to H. Fikentscher in aqueous solution at 25° C., a pH of 7 and a polymer concentration of the Na salt of 1% by weight) and contain, as copolymerized units, (a) from 99 to 15 mol % of one or more monoethylenically unsaturated $C_3$–$C_6$ monocarboxylic acids, (b) from 0.5 to 84.5 mol % of one or more monoethylenically unsaturated $C_4$–$C_6$-dicarboxylic acids, (c) from 0 to 20 mol % of one or more hydroxyalkyl esters, where hydroxyalkyl is of 2 to 6 carbon atoms, of monoethylenically unsaturated $C_3$–$C_6$-carboxylic acids, (d) from 0 to 30 mol % of other water-soluble, monoethylenically unsaturated monomers copolymerizable with (a), (b) and (c) and (e) from 0.5 to 15 mol % of one or more comonomers which possess two or more ethylenically unsaturated, nonconjugated double bonds and have one or more —CO—OX groups in which X is hydrogen, one equivalent of an alkali metal or alkaline earth metal or an ammonium group, with the proviso that the sum of the mol % (a) to (e) is always 100.

The present invention furthermore relates to water-soluble copolymers based on monoethylenically unsaturated carboxylic acids of 3 to 6 carbon atoms which have a K value of from 8 to 100 (determined on the Na salt according to H. Fikentscher in aqueous solution at 25° C., a pH of 7 and a polymer concentration of the Na result of 1% by weight) and which, in addition to (a) not less than 15 mol % of one or more monoethylenically unsaturated $C_3$–$C_6$-monocarboxylic acids, (b) from 0.5 to 84.5 mol % of one or more monoethylenically unsaturated $C_4$–$C_6$-dicarboxylic acids, (c) from 0 to 20 mol % of one or more hydroxyalkyl esters, where hydroxyalkyl is of 2 to 6 carbon atoms, of monoethylenically unsaturated $C_3$–$C_6$-carboxylic acids, (d) from 0 to 30 mol % of other water-soluble, monoethylenically unsaturated monomers copolymerizable with (a), (b) and (c) and (e) from 0.5 to 15 mol % of one or more comonomers which possess two or more ethylenically unsaturated, nonconjugated double bonds and have one or more —CO—OX groups in which X is hydrogen, one equivalent of an alkali metal or alkaline earth metal or an ammonium group, also contain (f) from 0.05 to 10 mol % of one or more comonomers which differ from (e) and possess two or more ethylenically unsaturated, nonconjugated double bonds, as copolymerized units, with the proviso that the sum of the mol % (a) to (f) is always 100.

The water-soluble copolymers are prepared by copolymerization of a monomer mixture of (a) from 99 to 15 mol % of one or more monoethylenically unsaturated $C_3$–$C_6$-monocarboxylic acids, (b) from 0.5 to 84.5 mol % of one or more monoethylenically unsaturated $C_4$–$C_6$-dicarboxylic acids, (c) from 0 to 20 mol % of one or more hydroxyalkyl esters, where hydroxyalkyl is of 2 to 6 carbon atoms, of monoethylenically unsaturated $C_3$–$C_6$-carboxylic acids and (d) from 0 to 30 mol % of other water-soluble, monoethylenically unsaturated monomers copolymerizable with (a), (b) and (c), in aqueous solution in the presence of a polymerization initiator, with the proviso that the copolymerization is carried out in the presence of (e) from 0.5 to 15 mol % of one or more comonomers which possess two or more ethylenically unsaturated, nonconjugated double bonds and have one or more —CO—OX groups in which X=H, one equivalent of an alkali metal or alkaline earth metal or an ammonium group, the sum of the mol % (a) to (e) always being 100.

If the water-soluble copolymers also contain monomers of group (f), they are prepared by copolymerization of a monomer mixture of (a) not less than 15 mol % of a monoethylenically unsaturated $C_3$–$C_6$-monocarboxylic acid, (b) from 0.5 to 84.5 mol % of a monoethylenically unsaturated $C_4$–$C_6$-dicarboxylic acid, (c) from 0 to 20 mol % of one or more hydroxyalkyl esters, where hydroxyalkyl is of 2 to 6 carbon atoms, monoethylenically unsaturated $C_3$–$C_6$-carboxylic acids and (d) from 0 to 30 mol % of other water-soluble, monoethylenically unsaturated monomers copolymerizable with (a), (b) and (c), in aqueous solution and in the presence of a polymerization initiator and a regulator, the copolymerization being carried out in the presence of (e) from 0.5 to 15 mol % of one or more comonomers which possess two or more ethylenically unsaturated, nonconjugated double bonds and have one or more —CO—OX groups in which X is hydrogen, one equivalent of an alkali metal or alkaline earth metal or an ammonium group and (f) from 0.05 to 10 mol % of one or more comonomers which differ from (e) and possess two or more ethylenically unsaturated, nonconjugated double bonds, with the proviso that the sum of the mol % (a) to (f) is always 100.

Suitable components (a) of the water-soluble copolymers are monoethylenically unsaturated $C_3$–$C_6$-monocarboxylic acids. Examples of suitable carboxylic acids of this type are acrylic acid, methacrylic acid, ethacrylic acid, vinylacetic acid, allylacetic acid and crotonic acid. Acrylic acid and/or methacrylic acid are preferably used as monomers of component (a). The monomers of component (a) are present in the copolymer in an amount of from 99 to 15, preferably from 90 to 20, mol %.

Monoethylenically unsaturated $C_4$–$C_6$-dicarboxylic acids are used as monomers of component (b). These are, for example, maleic acid, itaconic acid, citraconic acid, mesaconic acid, fumaric acid and methylenemalonic acid. Maleic acid or itaconic acid is preferably used as monomer (b). The monomers (b) are present in the copolymers in an amount of from 0.5 to 84.5, preferably from 5 to 60, mol %.

The copolymers may contain, as copolymerized components (c), hydroxyalkyl esters, where hydroxyalkyl is of 2 to 6 carbon atoms, of monoethylenically unsaturated $C_3$–$C_6$-carboxylic acids. The hydroxyalkyl ester groups of this group of monomers are derived from polyhydric alcohols, e.g. glycol, glycerol, propane-1,2-diol, propane-1,3-diol, butane-1,4-diol, butane-1,3-diol, butane-2,3-diol, mixtures of butanediols or propanediols, hexane-1,6-diol or neopentylglycol. The polyhydric alcohols are esterified with monoethylenically unsaturated $C_3$–$C_6$-carboxylic acids. These are the carboxylic acids stated above under (a) and (b). Hence, examples of suitable components (c) are hydroxyethyl acrylate, hydroxyethyl methacrylate, hydroxy-n-propyl methacrylate, hydroxy-n-propyl acrylate, hydroxyisopropyl acrylate, hydroxyisopropyl methacrylate, hydroxy-n-butyl acrylate, hydroxyisobutyl acrylate, hydroxy-n-butyl methacrylate, hydroxyisobutyl methacrylate, hydroxyethyl monomaleate, hydroxyethyl dimaleate, hydroxypropyl monomaleate, hydroxypropyl dimaleate, hydroxy-n-butyl monomaleate, hydroxy-n-butyl dimaleate and hydroxyethyl monoitaconate. Among the hydroxyalkyl esters of the monoethylenically unsaturated dicarboxylic acids, both the monoesters and the diesters of the dicarboxylic acids with the abovementioned polyhydric alcohols are suitable.

Hydroxyethyl acrylate, hydroxyethyl methacrylate, butane-1,4-diol monoacrylate and the industrial mixtures of hydroxypropyl acrylates are preferably used as component (c). The isomer mixtures of 2-hydroxy-1-propyl acrylate and 1-hydroxy-2-propyl acrylate are of particular industrial importance here. These hydroxyalkyl acrylates are prepared by reacting acrylic acid with propylene oxide. The monomers of group (c) are present in polymerized form in the copolymer in an amount of from 0 to 20, preferably from 0 to 15, mol %.

The copolymers may contain, as component (d), other water-soluble monoethylenically unsaturated monomers which are copolymerizable with the other monomers. Examples of suitable monomers of this type are acrylamide, methacrylamide, 2-acrylamido-2-methylpropanesulfonic acid, vinylsulfonic acid, allylsulfonic acid, vinylphosphonic acid, allylphosphonic acid, acrylonitrile, methacrylonitrile, dimethylaminoethyl acrylate, diethylaminoethyl acrylate, diethylaminoethyl methacrylate, N-vinylpyrrolidone, N-vinylformamide, N-vinylimidazole, N-vinylimidazoline, 1-vinyl-2-methyl-2-imidazoline, vinyl acetate and mixtures of the stated monomers. Those monomers of this group which contain acid groups can be used in the copolymerization in the form of the free acid groups, or in a form partially or completely neutralized with alkali metal bases or ammonium bases. The basic acrylates, such as diethylaminoethyl acrylate, are neutralized or quaternized with acids and then subjected to the copolymerization. The monomers (d) are present in the copolymers in an amount of from 0 to 30, preferably from 0 to 20, mol %. They serve merely to modify the copolymers.

On the other hand, the monomers of component (e) constitute an important part of the copolymers. These are comonomers which possess two or more ethylenically unsaturated, nonconjugated double bonds and one or more —CO—OH groups and/or their salt with an alkali metal, ammonium or alkaline earth metal base. These comonomers increase the molecular weight of the copolymers and are present in the copolymers in an amount of from 0.5 to 15, preferably from 1 to 12, mol %.

The comonomers (e) are obtainable by reacting (e1) maleic anhydride, itaconic anhydride or citraconic anhydride, or a mixture of these, with (e2) polyhydric alcohols of 2 to 6 carbon atoms, water-soluble or water-insoluble polyalkylene glycols having a molecular weight of up to about 400, water-soluble polyalkylene glycols having a molecular weight of from above about 400 to 10,000, polyglycerols having a molecular weight of up to 2,000, diamines, polyalkylenepolyamines, polyethyleneimines, aminoalcohols, hydroxyamino- or -diaminocarboxylic acids, in particular lysine and serine, water-soluble copolymers of ethylene oxide and carbon dioxide, polyvinyl alcohol having a molecular weight of up to 10,000, allyl alcohol, allylamine, hydroxyalkyl esters, where hydroxyalkyl is of 2 to 6 carbon atoms, of monoethylenically unsaturated $C_3$–$C_6$-carboxylic acids or of saturated $C_3$–$C_6$-hydroxycarboxylic acids, or mixtures of these.

Polyhydric alcohols of 2 to 6 carbon atoms are, for example, glycol, glycerol, pentaerythritol and monosaccharides, such as glucose, mannose or galactose, uronic acids, such as galacturonic acid, and sugar acids, such as mucic acid or galactonic acid.

Water-soluble polyalkylene glycols are the adducts of ethylene oxide, propylene oxide, n-butylene oxide and isobutylene oxide, or a mixture of these, with polyhydric alcohols of 2 to 6 carbon atoms, for example the adducts of ethylene oxide with glycol, adducts of ethylene oxide with glycerol, adducts of ethylene oxide with pentaerythritol, adducts of ethylene oxide with monosaccharides, and adducts of mixtures of the stated alkylene oxides with polyhydric alcohols. These adducts may be block copolymers of ethylene oxide and propylene oxide, of ethylene oxide and butylene oxides or of ethylene oxide, propylene oxide and butylene oxides. In addition to the block copolymers, adducts which contain the stated alkylene oxides randomly distributed as copolymerized units are also suitable.

The molecular weight of the polyalkylene glycols is advantageously up to 5,000, preferably up to 2,000. Among the water-soluble polyalkylene glycols, diethylene glycol, triethylene glycol, tetraethylene glycol and polyethylene glycol having a molecular weight of up to 1,500 are preferably used.

Other suitable components (e2) are polyglycerols having a molecular weight of up to 2,000. From this class of substances, diglycerol, triglycerol and tetraglycerol are preferably used.

Examples of preferred polyamines are diamines, such as ethylenediamine, 1,3-propylenediamine, 1,4-butylenediamine, 1,6-hexamethylenediamine and melamine. Examples of suitable polyalkylenepolyamines are diethylenetriamine, triethylenetetramine, pentaethylenehexamine, N-(3-aminopropyl)-1,3-propanediamine and 3-(2-aminoethyl)aminopropylamine. Particularly suitable polyethyleneimines have a molecular weight of up to 5,000.

Other suitable components (e2) are aminoalcohols, such as ethanolamine, 2-aminopropan-1-ol, neopentanolamine and 1-methylamino-2-propanol.

Further suitable components (e2) are water-soluble copolymers of ethylene oxide and carbon dioxide, which are obtainable by copolymerization of ethylene oxide and carbon dioxide. Polyvinyl alcohols having a molecular weight of up to 10,000, preferably polyvinyl alcohols having a molecular weight of up to 2,000, are also suitable. The polyvinyl alcohols which are prepared from polyvinyl acetate by hydrolysis may be partially or completely hydrolyzed. Other suitable compounds of component (e2) are lysine, serine, allyl alcohol, allylamine and hydroxyalkyl esters, where hydroxyalkyl is of 2 to 6 carbon atoms, of monoethylenically unsaturated $C_3$–$C_6$-mono- and dicarboxylic acids. Compounds of this type have already been described above in another context, i.e. as monomers of component (c). Hydroxyalkyl esters of saturated $C_3$–$C_6$-hydroxycarboxylic acids, such as glycol (mono)hydroxyacetate, glycol (mono)lactate or neopentylglycol (mono)hydroxypivalate.

Comonomers (e) of maleic anhydride and ethylene glycol, polyethylene glycol having a molecular weight of up to 2,000, glycerol, diglycerol, triglycerol, tetraglycerol, and polyglycerols having a molecular weight of up to 2,000, pentaerythritol, monosaccharides, neopentylglycol, $\alpha,\omega$-diamines of 2 to 6 carbon atoms, $\alpha,\omega$-diols of 3 to 6 carbon atoms and neopentylglcyol hydroxypivalate are preferably used. Comonomers (e) which are derived from ethylene glycol and $\alpha,\omega$-diols can be described, for example, by the formula:

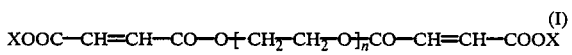  (I)

where X is H, an alkali metal or an ammonium group and n is from 1 to 120, preferably up to 50.

Comonomers (e) which, for example, are formed by reacting maleic anhydride with $\alpha,\omega$-diamines can be characterized, for example, by the formula

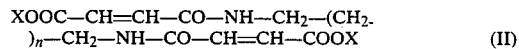  (II)

where X is H, an alkali metal or an ammonium group and n is from 0 to 4.

The water-soluble copolymers are prepared by copolymerization of a monomer mixture of (a) from 99 to 15 mol % of one or more monoethylenically unsaturated $C_3$–$C_6$-monocarboxylic acids, (b) from 0.5 to 84.5 mol % of one or more monoethylenically unsaturated $C_4$–$C_6$-dicarboxylic acids, (c) from 0 to 20 mol % of one or more hydroxyalkyl esters, where hydroxyalkyl is of 2 to 6 carbon atoms, of monoethylenically unsaturated $C_3$–$C_6$-carboxylic acids and (d) from 0 to 30 mol % of other water-soluble, monoethylenically unsaturated monomers copolymerizable with (a), (b) and (c), in aqueous solution in the presence of a polymerization initiator and, according to the invention, additionally in the presence of (e) 0.5 to 15 mol % of a comonomer which possesses two or more ethylenically unsaturated, nonconjugated double bonds and one or more —CO—OH groups and/or their salt with an alkali metal, ammonium or alkaline earth metal base.

The sum of the mol % of components (a) to (e) is always 100. The copolymerization is carried out in an aqueous medium, preferably in a purely aqueous medium. It may be effected by various procedures; for example, the monomers (a) to (e) can be polymerized batchwise in the form of aqueous solutions. It is also possible initially to take some of the monomers and some of the initiator in the polymerization reactor and to heat them to the polymerization temperature under an inert gas atmosphere and then to add the remaining monomers and the initiator to the reactor at the rate at which the polymerization progresses. The polymerization temperatures are from 20° to 200° C., preferably from 50° to 150° C. At above 100° C., pressure apparatuses are used.

In a preferred embodiment of the present invention process, the comonomer (e) is first prepared by a method in which (e1) maleic anhydride, itaconic anhydride, citraconic anhydride or a mixture of these is initially taken in a reactor and is reacted therein with (e2) polyhydric alcohols of 2 to 6 carbon atoms, water-soluble or water-insoluble polyalkylene glycols having a molecular weight of up to about 400, water-soluble polyalkylene glycols having a molecular weight of from above about 400 to 10,000, polyglycerols having a molecular weight of up to 2,000, diamines, polyalkylenepolyamines, polyethyleneimines, aminoalcohols, lysine, serine, water-soluble copolymers of ethylene oxide and carbon dioxide, polyvinyl alcohol having a molecular weight of up to 10,000, allyl alcohol, allylamine, hydroxyalkyl esters, where hydroxyalkyl is of 2 to 6 carbon atoms, of monoethylenically unsaturated $C_3$–$C_6$-carboxylic acids or of saturated $C_3$–$C_6$-hydroxycarboxylic acids or mixtures of these, at from 50° to 200° C. This reaction is preferably carried out in the absence of water, although small amounts of water do not present any problems when an appropriate excess of component (e1) is used. Instead of the compounds stated under (e1), it is however also possible to use the mono- or diesters with $C_1$–$C_4$-alcohols, the said esters being derived therefrom. In these cases, transesterification or amidation is carried out, and the resulting $C_1$–$C_4$-alcohol is preferably distilled off from the reaction mixture. Where amino-containing compounds stated under (e2) are used, the corresponding amides are formed in the reaction with the mono- or diesters of the anhydrides described under (e1). If, in the preparation of the comonomers (e), esters of component (e1) are used, these esters are preferably dimethyl maleate, monomethyl maleate, dimethyl itaconate, monoisopropyl maleate and diisopropyl maleate. If necessary, conventional esterification catalysts may also be used.

Not less than 0.5 mol of a compound of component (e1) is used per mol of the compounds (e2). The temperature during the reaction is preferably from 50° to 150° C. The reaction is carried out until conversion of the component (e2) is virtually quantitative. Component (e1), which is usually used in excess, can remain in the reaction mixture after the preparation of the comonomer is complete. In this case, the comonomer may be dissolved in a monoethylenically unsaturated $C_3$–$C_6$-monocarboxylic acid and then subjected to the copolymerization together with the unconverted part of component (e1) and the other monomers. Since the copolymerization is carried out in an aqueous medium, the excess dicarboxylic anhydride (e1) still present in the comonomer is hydrolyzed to the corresponding dicarboxylic acid. This dicarboxylic acid is then considered as comonomer (b).

The initially prepared comonomer (e), which still contains excess dicarboxylic anhydride, may however also remain in the reaction mixture in which it was prepared and may be dissolved therein initially by adding water or dilute aqueous sodium hydroxide solution. During this procedure, dicarboxylic anhydride still present is hydrolyzed. This monomer mixture is then copolymerized by adding the other comonomers. The copolymerization of monomers (a) to (e) is carried out at a pH of the aqueous solution of from 2 to 9, preferably from 3 to 7. The monomers (a), (b) and (e), each of which contains carboxylic acid groups, can be copolymerized in the form of the free carboxylic acids or in neutralized, preferably partially neutralized, form, the degree of neutralization being from 0 to 100, preferably from 40 to 90, mol %. The neutralization is preferably carried out using alkali metal or ammonium bases. These are, for example, sodium hydroxide solution, potassium hydroxide solution, sodium carbonate, potassium carbonate or ammonium bases, such as ammonia, $C_1$-$C_{18}$-alkylamines, dialkylamines, such as dimethylamine, di-n-butylamine or dihexylamine, tertiary amines, such as trimethylamine, triethylamine, tributylamine or triethanolamine, and quaternized nitrogen bases, e.g. tetramethylammonium hydroxide, tetramethyllaurylammonium hydroxide and tetramethylbenzylammonium hydroxide. Sodium hydroxide solution, potassium hydroxide solution or ammonia is preferably used for neutralization. However, the neutralization may also be carried out using alkaline earth metal bases, e.g. Ca hydroxide or $MgCO_3$.

Preferably used polymerization initiators are water-soluble compounds which form free radicals, for example hydrogen peroxide, peroxydisulfates and mixtures of hydrogen peroxide and peroxydisulfates. Examples of suitable peroxydisulfates are lithium peroxydisulfate, sodium peroxydisulfate, potassium peroxydisulfate and ammonium peroxydisulfate. In the case of mixtures of hydrogen peroxide and peroxydisulfate, any ratio may be employed; preferably, hydrogen peroxide and peroxydisulfate are used in a weight ratio of from 3:1 to 1:3. Mixtures of hydrogen peroxide and sodium peroxydisulfate are preferably used in a weight ratio of 1:1. The abovementioned water-soluble polymerization initiators can, if required, also be used in combination with reducing agents, e.g. iron(II) sulfate, sodium sulfite, sodium bisulfite, sodium dithionite, triethanolamine and ascorbic acid, in the form of redox initiators. Examples of suitable water-soluble organic peroxides are acetylacetone peroxide, methyl ethyl ketone peroxide, tert-butyl hydroperoxide and cumene hydroperoxide. Furthermore, the water-soluble organic peroxides can be used with the abovementioned reducing agents. Other water-soluble polymerization initiators are azo initiators, e.g. 2,2'-azobis-(2-amidinopropane) dihydrochloride, 2,2'-azobis-(N,N'-dimethylene)isobutyramidine dihydrochloride, 2-(carbamylazo)-isobutyronitrile and 4,4'-azobis-(4-cyanovaleric acid). The polymerization can also be initiated using water-insoluble initiators, such as dibenzoyl peroxide, dicyclohexyl peroxydicarbonate, dilauryl peroxide or azobisisobutyronitrile.

The initiators are used in amounts of from 0.1 to 10, preferably from 0.5 to 7, % by weight, based on the sum of the monomers used in the polymerization. The polymerization initiators can be added continuously or batchwise to the polymerizing mixture, either together with the monomers or separately from these, in the form of aqueous solutions.

The copolymerization may furthermore be carried out in the presence or absence of a regulator. Water-soluble compounds which are either infinitely miscible with water or dissolve therein in an amount of more than 5% by weight at 20° C. are preferably used for this purpose.

Compounds of this type are, for example, aldehydes of 1 to 4 carbon atoms, such as formaldehyde, acetaldehyde, propionaldehyde, n-butyraldehyde and isobutyraldehyde, formic acid, ammonium formate, hydroxylammonium salts, in particular hydroxylammonium sulfate, SH-containing compounds of up to 6 carbon atoms, such as thioglycolic acid, mercaptoalcohols, such as mercaptoethanol, mercaptopropanol, mercaptobutanols and mercaptohexanol, monohydric and polyhydric alcohols of not more than 6 carbon atoms, such as isopropanol, glycol, glycerol and isobutanol. Preferred regulators are water-soluble mercaptans, ammonium formate and hydroxylammonium sulfate. The regulators are used in amounts of from 0 to 25% by weight, based on the sum of the monomers used in the polymerization. The particularly effective regulators, which are preferred, are used in amounts of not more than 15% by weight. If the reaction is carried out in the presence of regulators, the minimum amount used is 0.2% by weight, based on the monomers to be polymerized.

In the novel process, monomer mixtures of
(a) from 99 to 15 mol % of acrylic acid, methacrylic acid or a mixture of these,
(b) from 0.5 to 84.5 mol % of maleic acid and/or itaconic acid and
(c) from 0 to 20 mol % of hydroxypropyl acrylates, hydroxypropyl methacrylates, hydroxyethyl acrylate, hydroxyethyl methacrylate, hydroxybutyl acrylates or hydroxybutyl methacrylates, or a mixture of these, and
(e) from 0.5 to 15 mol % of a comonomer of (e1) maleic anhydride and (e2) ethylene glycol, polyethylene glycol having a molecular weight of up to 2,000, glycerol, polyglycerols having a molecular weight of up to 2,000, pentaerythritol, monosaccharides, neopentylglycol, α, ω-diamines of 2 to 6 carbon atoms, α,ω-diols of 3 to 6 carbon atoms, neopentylglycol hydroxypivalate or a mixture of these compounds are preferably polymerized.

The preparation of copolymers of
(a) acrylic acid and/or methacrylic acid
(b) maleic acid and
(e) one of the abovementioned comonomers of the formula (I) or (II)
is particularly preferred.

The water-soluble copolymers described above may furthermore be modified in such a way that they contain up to 10 mol % of a comonomer of group (f) as copolymerized units. Compounds which possess two or more ethylenically unsaturated double bonds and do not fall under the definition of the compounds of group (e) are used as comonomer (f). Suitable comonomers (f) are, for example, N,N'-methylenebisacrylamide, polyethylene glycol diacrylates and polyethylene glycol dimethacrylates, each of which is derived from polyethylene glycols having a molecular weight of from 106 to 4000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, adducts of ethylene oxide and/or propylene oxide with trimethylolpropane, the said adducts being diesterified or triesterified with acrylic acid or methacrylic acid, polyhydric alcohols which are diesterified or polyesterified with acrylic acid or methacrylic acid, such as glycerol or pentaerythritol, triallylamine, tetraallylethylenediamine, divinylbenzene, diallyl phthalate, polyethylene glycol divinyl ether, trimethylolpropane diallyl ether, butanediol divinyl ether, pentaerythritol triallyl ether and/or divinylethyleneurea. Examples of preferably used water-soluble comonomers (f) are N,N'-methylenebisacrylamide, polyethylene glycol diacrylates, polyethylene glycol dimethacrylates, pentaerythritol triallyl ether and/or divinylurea.

If the comonomers of group (f) are incorporated in the polymers, from 0.05 to 10, preferably from 0.1 to 6, mol %, based on the monomers present in the copolymerization, of the said comonomers are employed.

Water-soluble copolymers of this type are prepared by copolymerization of monomer mixtures of (a) not less than 15 mol % of one or more monoethylenically unsaturated $C_3$–$C_6$-monocarboxylic acids, (b) from 0.5 to 84.5 mol % of one or more monoethylenically unsaturated $C_4$–$C_6$-dicarboxylic acids, (c) from 0 to 20 mol % of one or more hydroxyalkyl esters, where hydroxyalkyl is of 2 to 6 carbon atoms, of monoethylenically unsaturated $C_3$–$C_6$-carboxylic acids and (d) 0 to 30 mol % of other water-soluble, monoethylenically unsaturated monomers copolymerizable with (a), (b) and (c) in aqueous solution in the presence of a polymerization initiator and regulator, and additionally in the presence of (e) from 0.5 to 15 mol % of a comonomer which possesses two or more ethylenically unsaturated, nonconjugated double bonds and one or more —CO—OH groups and/or their salt with an alkali metal, ammonium or alkaline earth metal base, and (f) from 0.05 to 10 mol % of one or more comonomers which differ from (e) and possess two or more ethylenically unsaturated, nonconjugated double bonds.

The sum of the mol % of components (a) to (f) is always 100. The copolymerization is carried out in an aqueous medium, preferably in a purely aqueous medium. It can be effected by various procedures; for example, the monomers (a) to (f) can be polymerized batchwise in the form of aqueous solutions. Furthermore, it is possible initially to take some of the monomers and some of the initiator in the polymerization reactor and to heat these to the polymerization temperature under an inert gas atmosphere, and then to add the remaining monomers and the initiator to the reactor at the rate at which the polymerization progresses. The polymerization temperatures are from 20° to 200° C., preferably from 50° to 150° C. At above 100° C., pressure apparatuses are used.

In a preferred embodiment of the preparation process, the comonomer (e) is first prepared as described above. The initiators stated above are used in amounts of up to 30, preferably from 10 to 25, % by weight, based on the sum of the monomers used in the polymerization. The polymerization initiators can be added continuously or batchwise to the polymerizing mixture, either together with the monomers or separately from these, in the form of aqueous solutions.

The copolymerization of the monomers (a) to (f) is carried out in the presence of a regulator. Water-soluble compounds which are either infinitely miscible with water or dissolve therein in an amount of more than 5% by weight at 20° C. are preferably used for this purpose. Compounds of this type are, for example, aldehydes of 1 to 4 carbon atoms, such as formaldehyde, acetaldehyde, propionaldehyde, n-butyraldehyde and isobutyraldehyde, formic acid, ammonium formate, hydroxylammonium salts, in particular hydroxylammonium sulfate, SH-containing compounds of not more than 6 carbon atoms, such as thioglycolic acid, mercaptoalcohols, such as mercaptoethanol, mercaptopropanol, mercaptobutanols and mercaptohexanol, and monohydric and polyhydric alcohols of not more than 6 carbon atoms, such as isopropanol, glycol, glycerol and isobutanol. Preferred regulators are water-soluble mercaptans, ammonium formate and hydroxylammonium sulfate. The regulators are used in amounts of from 0.2 to 25% by weight, based on the sum of the monomers used in the polymerization. The particularly effective regulators, which are preferred, are used in amounts of not more than 15% by weight.

In the novel process, where monomers (f) are used, monomer mixtures of (a) not less than 15 mol % of acrylic acid, methacrylic acid or a mixture of these, (b) from 0.5 to 84.5 mol % of maleic acid and/or itaconic acid and (c) from 0 to 20 mol % of hydroxypropyl acrylates, hydroxypropyl methacrylates, hydroxyethyl acrylate, hydroxyethyl methacrylate, hydroxybutyl acrylates, hydroxybutyl methacrylates or a mixture of these, (e) from 0.5 to 15 mol % of a comonomer of (e1) maleic anhydride and (e2) ethylene glycol, polyethylene glycol having a molecular weight of up to 2,000, glycerol, polyglycerols having a molecular weight of up to 2,000, pentaerythritol, monosaccharides, neopentylglycol, $\alpha,\omega$-diamines of 2 to 6 carbon atoms, $\alpha,\omega$-diols of 3 to 6 carbon atoms, neopentylglycol hydroxypivalate or mixtures of these compounds and (f) from 0.05 to 10 mol % of polyethylene glycol diacrylates, polyethylene glycol dimethacrylates, ethylene glycol di(meth)acrylate, glycerol diacrylate and/or glycerol dimethacrylate are preferably polymerized.

The preparation of copolymers of (a) acrylic acid and/or methacrylic acid, (b) maleic acid, (e) one of the abovementioned comonomers of the formula (I) or (II) and (f) polyethylene glycol diacrylates which are derived from polyethylene glycol having a molecular weight of from 106 to 1500 is particularly preferred.

The copolymerization of the monomers (a) to (f) gives aqueous polymer solutions which have a polymer content of up to 70% by weight. It is of course also possible to prepare highly dilute, e.g. 1% strength, aqueous solutions, but for economic reasons the copolymerization is carried out in such a way that copolymer solutions of not less than 20% strength by weight are prepared. After the copolymerization, the solutions can be brought to a pH of from 6.5 to 7, unless the polymerization has in any case been carried out in this range. The copolymers can be obtained by evaporating down the aqueous solutions. They have a low residual monomer content and are surprisingly biodegradable. The biodegradability of the novel copolymers is up to 100% according to DIN 38,412, Part 24, Static Test (L25), and is as a rule from 20 to 95%.

The copolymers are water-soluble. If they are insoluble in water in the free acid form, they can be converted to a water-soluble form by partial or complete neutralization with NaOH, KOH, ammonia or amines. Copolymers or their alkali metal or ammonium salts which have a solubility of not less than 20 g per liter of water at 20° C. are regarded as water-soluble in the present context. The copolymers surprisingly have the advantage that, at low polymer concentrations, they do not show any precipitation in aqueous solutions containing copolymers, the residual monomer content and the data on biodegradability [determined according to DIN 38,412, Part 24, Static Test (L25)] of the copolymers.

TABLE 1

| | Preparation of the comonomer from the components | | Monomers used in the copolymerization | | | Copolymer | | Biodegradability [%] |
|---|---|---|---|---|---|---|---|---|
| No. | e1 [mole] | e2 [mole] | Acrylic acid [mol %] | MA [mol %] | Comonomer of (e1) + (e2) [mol %] | K valve | Residual content of maleic acid [% by weight] | |
| 1 | 1 MA[(1)] | 0.25 ethylene glycol | 84.2 | 10.5 | 5.3 | 64.2 | 0.21 | 45 |
| 2 | 1 MA | 0.25 neopentylglycol | 84.2 | 10.5 | 5.3 | 58.6 | 0.15 | 47 |
| 3 | 1 MA | 0.25 PEG$_{400}$[(2)] | 84.2 | 10.5 | 5.3 | 30.9 | 0.23 | 62 |
| 4 | 1 MA | 0.25 PEG$_{1500}$[(3)] | 84.2 | 10.5 | 5.3 | 25.2 | 0.30 | 89 |

[(1)]MA = maleic anhydride
[(2)]PEG$_{400}$ = polyethylene glycol having a molecular weight of 400
[(3)]PEG$_{1500}$ = polyethylene glycol having a molecular weight of 1500

Ca and/or Mg ions. Hence, it is possible to prepare stable solutions of the polymers in tap water without precipitation taking place.

The copolymers are used as coating agents for seed. In seed coating, where all cereal species, such as wheat, rye, oats and barley, as well as corn and lupins and other seed can be coated with a polymer film, more rapid germination of the seed is achieved compared with the uncoated seed. From 0.1 to 1 kg of the copolymers is used per 100 kg of seed. The copolymers are preferably sprayed onto the seed in the form of a dilute aqueous solution and form a protective polymer film on the seed. Finely divided, inert fillers, e.g. graphite, quartz, talc or bentonite, having a particle size of from 20 to 500 μm may be incorporated in the polymer film. The fillers are preferably applied together with the polymer solution to the material to be coated.

The K values stated in the examples were determined according to H. Fikentscher, Cellulosechemie, 13 (1932), 58–64 and 71–74; $K = k \times 10^3$. The measurements were carried out on sodium salt in aqueous solution at 25° C., a pH of 7 and a polymer concentration of the Na salt of 1% by weight. Where novel copolymers are obtained in the form of other salts or of the free acids, they must first be converted to the Na salts before the K value is determined. The molecular weights stated in the examples refer to the number average molecular weight.

EXAMPLE 1

98 g (1 mole) of maleic anhydride and 0.1 g of p-toluenesulfonic acid are initially taken in a 2 l glass reactor equipped with a stirrer, a thermometer, a nitrogen inlet, a condenser and three feed vessels, and are heated, together with 0.25 mole of a diol stated in Table 1, at 60° C. for 45 minutes. Thereafter, 200 ml of water are added to the melt, and the solution is heated for 30 minutes at 90° C. while passing in nitrogen and stirring.

The copolymerization is carried out in the following manner: 1075 g of a 35% strength sodium acrylate solution (4 moles) are added to the above mixture of comonomer and maleic acid at 90° C. in the course of 5 hours and, simultaneously with this, 55 g of 30% strength hydrogen peroxide which is dissolved in 45 ml of water are added over a period of 6 hours, separately from the monomer feed. A viscous solution is obtained, which is further polymerized for 1 hour after the end of the addition of the polymerization initiator, at 90° C. and while stirring. The solution is then cooled and is brought to pH 6.5 by adding 25% strength aqueous sodium hydroxide solution. Table 1 states the particular monomers used and the K values of the water-soluble copolymers, the residual monomer content and the data on biodegradability [determined according to DIN 38,412, Part 24, Static Test (L25)] of the copolymers.

The precipitation behavior of the copolymers stated under 1, 3 and 4 was tested at pH 7.5 in aqueous solutions which contained from 10 to 10,000 mg/l of Ca ions (as CaCl$_2$) (the following CA ion concentrations were tested: 10, 50, 75, 100, 150, 500, 1000 and 10,000 mg/l; the polymer concentrations were varied from 0.1 to 7 mg/l; 0.1, 0.5, 1.0, 2, 3, 4 and 7 mg/l were tested). No precipitation took place even after 20 days, whereas the copolymer of 30% by weight of maleic acid and 70% by weight of acrylic acid (K value 60) always gave precipitates under the abovementioned test conditions.

EXAMPLE 2

In a 2 l glass reactor equipped with a stirrer, a thermometer, a nitrogen inlet and three feed vessels, one of which is heatable and stirrable, 98 g (1 mole) of maleic anhydride are dissolved in each case in 500 ml of 4 molar aqueous sodium hydroxide solution and heated to 90° C. At the same time, 0.1 g of p-toluenesulfonic acid and the polyhydric alcohols stated in each case in Table 2 are added to 98 g (1 mole) of maleic anhydride in the heatable feed vessel and melted under a nitrogen atmosphere in the course of from 0.5 to 3.5 hours at from 60° to 120° C.

The copolymerization is carried out at 90° C. in the course of 5 hours by running in 285 g (3 moles) of sodium acrylate dissolved in 500 ml of water, and the melt of the comonomers (consisting of maleic anhydride and polyhydric alcohol and unreacted maleic anhydride) and, over a period of 6 hours, beginning with the monomer feed, and likewise continuously, 90 g of 30% strength hydrogen peroxide solution in 100 ml of water. A viscous aqueous solution is obtained, which is polymerized for a further hour after the end of the initiator addition, at 90° C. The aqueous solution is cooled and then brought to pH 6.5 with 25% strength aqueous sodium hydroxide solution. The substances used, the K values, the residual maleic acid content and the data on the biodegradability of the copolymers are shown in Table 2.

The biodegradability of the copolymers described in Table 2 was additionally demonstrated by experiments on bacterial growth. For this purpose, a concentration medium was prepared on solid nutrient substrates and solidified with 18 g/l of agar. The concentration medium had the following composition:

| | |
|---|---|
| disodium hydrogen phosphate dihydrate | 7 g/l |
| potassium dihydrogen phosphate | 3 g/l |
| sodium chloride | 0.5 g/l |

|                                | -continued |
|---|---|
| ammonium chloride | 1.0 g/l |
| solution of trace elements | 2.5 ml/l pH 7.0 |
| (prepared according to T. Bauchop and S.R. Elsden, J. |  |
| gen. Mikrobiol. 23 (1960), 457–469). |  |

The compolymers to be tested are added to the nutrient media in concentrations of 10 g/l.

Soil samples were either introduced into a liquid medium and shaken there for 7 days at 30° C. or introduced in the form of an aqueous suspension directly onto solid nutrient substrates and likewise incubated at 30° C. The concentration cultures in the liquid medium were transferred to solid nutrient substrates after 7 days. Readily growing colonies were removed from these plates and were tested for uniformity in a thin smear.

Pure bacteria cultures which exhibit clear growth on all copolymers shown in Table 2 were isolated in this manner.

When the bacterial growth experiments described above were carried out for comparison, using a copolymer of 30% by weight maleic acid and 70% by weight of acrylic acid (K value 60), there was no detectable bacterial growth.

which is heatable and stirrable, 98 g (1 mole) of maleic anhydride are dissolved in 500 ml of 4 molar aqueous sodium hydroxide solution and heated to 90° C. with the addition of 24.5 g of hydroxylammonium sulfate. At the same time, 0.4 mole of each of the diols stated in Table 3 and 0.1 g of p-toluenesulfonic acid are added to 98 g (1 mole) of maleic anhydride in the heatable feed vessel, and melted under nitrogen at 60° C. for 60 minutes. The melt is cooled to 20° C. and dissolved in 86 g (1 mole) of methacrylic acid.

285 g (3 moles) of sodium acrylate dissolved in 500 ml of water and the comonomer solution prepared in the heatable feed vessel (with comonomer still contains excess maleic anhydride and is dissolved in methacrylic acid) are added simultaneously, and in each case continuously, to the initially taken mixture heated at 90° C., in the course of 5 hours, and, likewise beginning with the monomer feed, 90 g of 30% strength hydrogen peroxide dissolved in 100 ml of water are added in the course of 6 hours. During the copolymerization, the reaction mixture is stirred and flushed with nitrogen. The viscous solution is further polymerized for 1 hour in each case at 95° C. and, after cooling to 30° C., is brought to pH 6.5 with 25% strength aqueous sodium hydroxide

TABLE 2

| Preparation of the comonomer in the feed vessel from the components | | Tempera-ture [°C.] | Reaction time [h] | Copolymerization | | | Copolymer | | |
|---|---|---|---|---|---|---|---|---|---|
| e1 [mole] | e2 [mole] | | | Acrylic acid [mol %] | Maleic acid (initially taken and from the feed) [mol %] | Comonomer of e1 + e2 [mol %] | K valve | Residual content of maleic acid [% by weight] | Biodegradability [%] |
| 1 MA | 0.25 ethylene glycol | 60 | 0.5 | 63.1 | 31.6 | 5.3 | 31.8 | 0.20 | 77 |
| 1 MA | 0.25 butanediol | 60 | 0.75 | 63.1 | 31.6 | 5.3 | 36.7 | 0.18 | 79 |
| 1 MA | 0.25 neopentyl-glycol | 60 | 0.75 | 63.1 | 31.6 | 5.3 | 36.7 | 0.21 | 83 |
| 1 MA | 0.25 HPN[(1)] | 100 | 1.5 | 63.1 | 31.6 | 5.3 | 30.3 | 0.23 | 85 |
| 1 MA | 0.25 diehtylene glycol | 100 | 1.0 | 63.1 | 31.6 | 5.3 | 27.6 | 01.5 | 84 |
| 1 MA | 0.25 PEG$_{400}$ | 90 | 2.0 | 63.1 | 31.6 | 5.3 | 40.2 | 0.30 | 63 |
| 1 MA | 0.25 glycerol | 80 | 3.0 | 62.5 | 33.3 | 4.2 | 36.2 | 0.26 | 78 |
| 1 MA | 0.125 diglycerol | 90 | 3.5 | 64.9 | 32.4 | 2.7 | 28.4 | 0.31 | 86 |
| 1 MA | 0.08 tetra-glycerol | 90 | 3.5 | 65.3 | 33.0 | 1.7 | 22.6 | 0.31 | 86 |
| 1 MA | 0.125 penta-erythritol | 100 | 3.5 | 64.9 | 32.4 | 2.7 | 37.6 | 0.24 | 88 |

[(1)]HPN = neopentylglycol monohydroxypivalate

EXAMPLE 3

In a 2 l glass reactor equipped with a stirrer, a thermometer, a nitrogen inlet and three feed vessels, one of solution. The starting materials used in each case and the K values of the copolymers, their residual content of maleic acid and the data on biodegradability are shown in Table 3.

TABLE 3

| Preparation of the comonomer in the feed vessel from the components | | Copolymerization of | | Comonomer (e) of (e1) + (e2) [mol %] | Copolymer | | |
|---|---|---|---|---|---|---|---|
| e1 [mole] | e2 [mole] | Component (a) [mol %] | Component (b) initially taken and from the feed [mole %] | | K value | Residual content of maleic acid [% by weight] | Biodegradability [%] |
| 1 MA | 0.4 ethylene glycol | 17.85 MAS[(1)] 53.50 AA[(2)] | 21.5 MS[(4)] | 7.15 | 23.1 | 0.19 | 81 |
| 1 MA | 0.4 neopentylglycol | 17.85 MAS 53.50 AA | 21.5 MS | 7.15 | 25.6 | 0.24 | 83 |
| 1 MA | 0.4 HPN[(3)] | 17.85 MAS 53.50 AA | 21.5 MS | 7.15 | 21.4 | 0.32 | 80 |
| 1 MA | 0.4 hexane-1,6-diol | 17.85 MAS | 21.5 MS | 7.15 | 22.9 | 0.15 | 76 |

TABLE 3-continued

| Preparation of the comonomer in the feed vessel from the components | | Copolymerization of | | Comonomer (e) of (e1) + (e2) [mol %] | Copolymer | | Biodegradability [%] |
|---|---|---|---|---|---|---|---|
| e1 [mole] | e2 [mole] | Component (a) [mol %] | Component (b) initially taken and from the feed [mole %] | | K value | Residual content of maleic acid [% by weight] | |
| | | 53.50 | | AA | | | |

(1)MAS = methacrylic acid
(2)AA = acrylic acid
(3)HPN = see Table 2
(4)MS = maleic acid

EXAMPLE 4

(a) Preparation of the comonomers A and B (component e)

A solution of 1.5 moles (147 g) of maleic anhydride in 350 g of dimethylformamide is initially taken in a 1 l glass reactor equipped with a stirrer, a condenser and a feed vessel. A solution of 1 mole of the diamine stated in each case in Table 4 and dissolved in 150 g of dimethylformamide is added to this solution, in each case at 40° C. over a period of 1.5 hours. The reaction temperature is kept at 60° C. When the addition of the diamine is complete, the resulting suspension is stirred for a further hour at 60° C. and then evaporated down, and the solid is filtered off. The filter cake is then boiled up briefly with acetone, the acetone is filtered off under suction and the filter cake is dried. The comonomers A and B obtainable in this manner are soluble in hot water. They have the structures shown above in formula (II). The yields of compounds of the formula (II) are from 72 to 91%.

(b) Copolymerization

In a 2 l glass reactor equipped with a stirrer, a thermometer, a nitrogen inlet, a condenser and 2 feed vessels, 49 g (0.5 mole) of maleic anhydride and 0.5 mole of the comonomer A or B prepared as described in (a) are initially taken, 300 ml of water are added and the stirred mixture is heated to 90° C. under a nitrogen atmosphere. The copolymerization is carried out as follows: 1075 g (4 moles) of a 35% strength aqueous sodium acrylate solution are added to the initially taken mixture in the course of 5 hours while stirring, and 33 g of 2,2'-azobis-(2-amidinopropane) dihydrochloride dissolved in 170 ml of water are added dropwise over a period of 6 hours at 90° C. under a nitrogen atmosphere. A viscous yellowish brown solution is obtained, which is further polymerized for 1 hour after the end of the initiator addition, at 90° C., and cooled to 30° C. and then brought to pH 6 with 25% strength aqueous sodium hydroxide solution. The starting materials, the substances used in the polymerization and the K values of the copolymers, their residual content of unpolymerized maleic acid and the data on biodegradability are shown in Table 4.

EXAMPLE 5

In a 2 l glass reactor equipped with a stirrer, a thermometer, a nitrogen inlet and 3 feed vessels, 1 of which is heatable and is provided with a stirrer, 98 g (1 mole) of maleic anhydride are dissolved in 500 ml of 4 molar aqueous sodium hydroxide solution and heated to 90° C. At the same time, 98 g (1 mole) of maleic anhydride are heated to 80° C. in a heatable feed vessel, and 0.4 mole of serine is added over a period of 2 hours. Thereafter, the excess maleic anhydride is hydrolyzed by adding 300 ml of water, and the resulting comonomer (component e) is dissolved in the added water, together with the maleic acid formed in the hydrolysis.

The copolymerization is carried out as follows: 282 g (3 moles) of sodium acrylate, dissolved in 500 ml of water, and the aqueous solution containing the comonomer and maleic acid are added dropwise in the course of 5 hours, while flushing with nitrogen, to the reactor contents heated at 90° C., this being followed by a dropwise addition of 90 g of 30% strength hydrogen peroxide, dissolved in 100 ml of water, in the course of 6 hours. The monomer mixture subjected to the copolymerization consists of 65.2 mol % of acrylic acid, 26.1 mol % of maleic acid and 8.7 mol % of the comonomer of maleic anhydride and serine. A viscous solution is obtained, which is further polymerized for 1 hour at 95° C., cooled to 35° C. and then brought to pH 6.5 with 25% strength aqueous sodium hydroxide solution. The copolymer has a K value of 33 and contains 0.19% by weight of unpolymerized maleic acid.

If Example 5 is repeated with the sole exception that 0.4 mole of lysine is used instead of the serine, a monomer mixture of 65.2 mol % of acrylic acid, 26.1 mol % of maleic acid and 8.7 mol % of a comonomer (reaction product of maleic anhydride and lysine) is likewise subjected to the copolymerization. This gives a copolymer having a K value of 30.1 and containing 0.21% by weight of unpolymerized maleic acid.

EXAMPLE 6

In a 2 l glass reactor equipped with a stirrer, a thermometer, a nitrogen inlet and 3 feed vessels, 98 g (1 mole) of maleic anhydride are dissolved in 500 ml of 4 molar aqueous sodium hydroxide solution and heated to

TABLE 4

| Comonomer | Acrylic acid component (a) [mol %] | Maleic acid component (b) [mol %] | ... Mol % of comonomer | Copolymer K value | Residual content of maleic acid [% by weight] | Biodegradability [%] |
|---|---|---|---|---|---|---|
| A(1) | 80 | 10 | 10 A | 43.0 | 0.19 | 35 |
| B(2) | 80 | 10 | 10 B | 40.1 | 0.21 | 38 |

(1)A = HOOC—CH=CH—CO—NH—CH$_2$—CH$_2$—NH—CO—CH=CH—COOH
(2)B = HOOC—CH=CH—CO—NH—CH$_2$—(CH$_2$)$_4$—CH$_2$—NH—CO—CH=CH—COOH

90° C. Out of 3 feed vessels, 1 feed vessel is heatable and is equipped with a stirrer. In this feed vessel, 98 g (1 mole) of maleic anhydride, 0.2 g of sodium acetate and 19.8 g (0.1 mole) of glucose monohydrate are heated at 120° C. for 2.5 hours while stirring. The conversion of maleic anhydride during the esterification is 50% after this time. The resulting melt is cooled and then dissolved in 72 g (1 mole) of acrylic acid.

For polymerization, 188 g (2 moles) of sodium acrylate, dissolved in 350 ml of water, and the solution of the comonomer of MA and glucose together with the excess maleic anhydride in acrylic acid are added dropwise to the initially taken mixture heated at 90° C., while flushing with nitrogen, and 90 g of 30% strength hydrogen peroxide, dissolved in 100 ml of water, are added dropwise in the course of 6 hours, the two feeds beginning at the same time. The viscous solution is further polymerized for 1 hour, cooled and then brought to pH 6.5 with 25% strength sodium hydroxide solution. The copolymer has a K value of 35.7 and contains 0.13% by weight of unpolymerized maleic acid. The biodegradability is 62%.

EXAMPLE 7

In a 2 l glass reactor equipped with a stirrer, a thermometer, a nitrogen inlet and 2 feed vessels, 147 g (1.5 mole) of maleic anhydride are dissolved in 500 ml of 6 molar aqueous sodium hydroxide solution and heated to 90° C.

For polymerization, 40.66 g (0.19 mole) of mono-2-hydroxyethyl acrylate maleate (comonomer, obtainable from maleic anhydride and 2-hydroxyethyl acrylate in a molar ratio of 1:1), dissolved in 162 g (2.25 moles) of acrylic acid, are then added dropwise in the course of 5 hours to the initially taken mixture heated at 90° C., while flushing with nitrogen, and 71.4 g of 30% strength hydrogen peroxide, dissolved in 28 g of water, are added dropwise in the course of 6 hours, the two feeds beginning at the same time. The monomer mixture which is subjected to the copolymerization contains 4.8 mol % of the comonomer of MA and 2-hydroxyethyl acrylate, 38.1 mol % of maleic acid and 57.1 mol % of acrylic acid. The viscous solution is further polymerized for 1 hour at 95° C., cooled to 28° C. and then brought to pH 6.5 with 25% strength aqueous sodium hydroxide solution. The copolymer has a K value of 42.2 and contains 0.19% by weight of unpolymerized maleic acid.

EXAMPLES 8 to 12

In a 4 glass reactor equipped with a stirrer, a thermometer, a nitrogen inlet and six feed vessels, one of which is heatable and stirrable, 1000 ml of water are initially taken and heated to 90° C. while flushing with nitrogen. In the heatable feed vessel IV, n moles of the monomer (e) stated in the table are melted together with m moles of maleic anhydride (MA) at 80° C. The other feed vessels are charged as follows:

Feed I: solution of p moles of the comonomer (f), stated in the table, in 2 moles of acrylic acid Feed II: 2 moles of acrylic acid Feed III: solution of q% by weight of regulator in 100 ml of water Feed V: 720 g of 25% strength aqueous sodium hydroxide solution Feed VI: 25 g of sodium persulfate dissolved in 500 ml of 30% strength $H_2O_2$.

At 90° C., and beginning at the same time, feeds I and III are metered in over 2 hours, feed IV in the course of 4 hours and feed VI in the course of 5½ hours. Two hours after the beginning of the monomer feed, feed II is added dropwise in the course of 2 hours and feed V is added dropwise in the course of 3 hours.

Thereafter, the reaction is allowed to continue for 1 hour and the mixture is cooled and brought to pH 7.

The amounts of comonomers (e) and (f) used in the examples, the amounts of acrylic acid (comonomer (a)), maleic anhydride and comonomer (e) and the regulators used (% by weight) and the K values of the copolymers obtained are shown in the table.

TABLE

| Example No. | Comonomer (a) [mole]; [mol %] | Comonomer (b) m[mole]; [mol %] | Comonomer (e) n[mole]; [mol %] | Comonomer (f) p[mole]; [mol %] | Regulator g [% by weight] | K value |
|---|---|---|---|---|---|---|
| 8 | acrylic acid 4; 86.0 | MA 0.15; 3.2 | ethylene glycol dimaleate 0.4; 8.6 | $PEG_{400}$ diacrylate 0.1; 2.2 | mercaptoethanol 5 | 38.8 |
| 9 | acrylic acid 4; 85.1 | MA 0.1; 2.1 | neopentylglycol dimaleate 0.4; 8.6 | ethylene glycol diacrylate 0.1; 2.2 | hydroxylammonium sulfate | 36.2 |
| 10 | acrylic acid 4; 83.3 | MA 0.2; 4.2 | $PEG_{300}$ dimaleate 0.4; 8.3 | glycerol diacrylate 0.2; 4.2 | mercaptoethanol 10 | 25.4 |
| 11 | acrylic acid 4; 80 | MA 0.3; 6 | tetramethylene glycol dimaleate 0.35; 7 | tetraethylene glycol diacrylate 0.2; 0.35 | mercaptoethanol 3 | 30.6 |
| 12 | acrylic acid 4; 82.5 | MA 0.45; 9.3 | diethylene glycol dimaleate 0.2; 4.1 | $PEG_{1500}$ diacrylate 0.2; 4.1 | mercaptoethanol 8 | 28.2 |

The biodegradability of the copolymers described in the table was demonstrated by bacterial growth experiments. For this purpose, a concentration medium was prepared on solid nutrient substrates and solidified with 18 g/l of agar. The concentration medium had the following composition:

| | |
|---|---|
| diodium hydrogen phosphate dihydrate | 7 g/l |
| potassium dihydrogen phosphate | 3 g/l |
| sodium chloride | 0.5 g/l |
| ammonium chloride | 1.0 g/l |
| solution of trace elements | 2.5 ml/l pH 7.0 |
| (prepared according to T. Bauchop and S.R. Elsden, J. gen. Mikrobiol. 23 (1960), 457–469). | |

The copolymers to be tested were added to the nutrient media in concentrations of 10 g/l.

Soil samples were either introduced into a liquid medium and shaken there for 7 days at 30° C. or introduced as an aqueous suspension directly onto solid nutrient substrates and likewise incubated at 30° C. The concentration cultures in the liquid medium were transferred to solid nutrient substrates after 7 days. Readily growing colonies were removed from these plates and tested for uniformity in a thin smear.

The pure bacterial cultures which show clear growth on all copolymers stated in the table were isolated in this manner.

When the bacterial growth experiments described above were carried out, for comparison, using a copolymer of 30% by weight of maleic acid and 70% by weight of acrylic acid (K value 60), no detectable bacterial growth was observed.

We claim:

1. A water-soluble copolymer based on monoethylenically unsaturated carboxylic acids of 3 to 6 carbon atoms, wherein the copolymer has a K value of from 8 to 100 (determined on the Na salt according to H. Fikentscher in aqueous solution at 25° C., a pH of 7 and polymer concentration of the Na salt of 1% by weight) and contains, as copolymerized units,
   (a) from 99 to 15 mol % of one or more monoethylenically unsaturated $C_3$–$C_6$-monocarboxylic acids,
   (b) from 0.5 to 84.5 mol % of one or more monoethylenically unsaturated $C_4$–$C_6$-dicarboxylic acids,
   (c) from 0 to 20 mol % of one or more hydroxyalkyl esters, where hydroxyalkyl is of 2 to 6 carbon atoms, of monoethylenically unsaturated $C_3$–$C_6$-carboxylic acids,
   (d) from 0 to 30 mol % of other water-soluble, monoethylenically unsaturated monomers copolymerizable with (a), (b) and (c) and
   (e) from 0.5 to 15 mol % of one or more comonomers which possess two or more ethylenically unsaturated, nonconjugated double bonds and one or more —CO—OX groups in which X is hydrogen, one equivalent of an alkali metal or alkaline earth metal or an ammonium group, with the proviso that the sum of the mol % (a) to (e) is always 100.

2. A water-soluble copolymer as claimed in claim 1, which contains, as copolymerized units,
   (a) not less than 15 mol % of one or more monoethylenically unsaturated $C_3$–$C_6$-monocarboxylic acids,
   (b) from 0.5 to 84.5 mol % of one or more monoethylenically unsaturated $C_4$–$C_6$-dicarboxylic acids,
   (c) from 0 to 20 mol % of one or more hydroxyalkyl esters, where hydroxyalkyl is of 2 to 6 carbon atoms, of monoethylenically unsaturated $C_3$–$C_6$-carboxylic acids,
   (d) from 0 to 30 mol % of other water-soluble, monoethylenically unsaturated monomers copolymerizable with (a), (b) and (c),
   (e) from 0.5 to 15 mol % of one or more comonomers which possess two or more ethylenically unsaturated, nonconjugated double bonds and one or more —CO—OX groups in which X is hydrogen, one equivalent of an alkali metal or alkaline earth metal or an ammonium group, and
   (f) from 0.05 to 10 mol % of one or more comonomers which differ from (e) and have two or more ethylenically unsaturated, nonconjugated double bonds, with the proviso that the sum of the mol % (a) to (f) is always 100.

3. A water-soluble copolymer as claimed in claim 1 or 2, wherein the copolymerized comonomer (e) is obtainable by reacting
   (e1) maleic anhydride, itaconic anhydride or citraconic anhydride, or a mixture of these with
   (e2) polyhydric alcohols of 2 to 6 carbon atoms, water-soluble or water-insoluble polyalkylene glycols having a molecular weight of up to 400, water-soluble polyalkylene glycols having a molecular weight from above about 400 to 10,000, polyglycerols having a molecular weight of up to 2,000, polyamines, polyalkylenepolyamines, polyethyleneimines, aminoalcohols, hydroxyamino- or -diaminocarboxylic acids, water-soluble copolymers of ethylene oxide and carbon dioxide, polyvinyl alcohol having a molecular weight of up to 10,000, allyl alcohol, allylamine, hydroxyalkyl esters, where hydroxyalkyl is of 2 to 6 carbon atoms, of monoethylenically unsaturated $C_3$–$C_6$-carboxylic acids or of saturated $C_3$–$C_6$-hydroxycarboxylic acids or mixtures of these.

4. A water soluble copolymer as claimed in claim 1, which contains, as copolymerizable units,
   (a) acrylic acid, methacrylic acid, or a mixture of both,
   (b) maleic acid, and
   (c) a compound of the formula

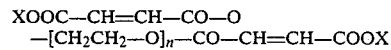
   XOOC—CH=CH—CO—O
   —[CH$_2$CH$_2$—O]$_n$—CO—CH=CH—COOX where X is H, an alkali metal, or an ammonium group and n is from 1 to 120.

5. A water soluble copolymer as claimed in claim 1, which contains, as copolymerizable units,
   (a) acrylic acid, methacrylic acid, or a mixture of both,
   (b) maleic acid, and
   (c) a compound of the formula

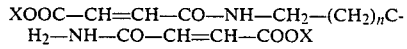
   XOOC—CH=CH—CO—NH—CH$_2$—(CH$_2$)$_n$CH$_2$—NH—CO—CH=CH—COOX where X is H, an alkali metal or an ammonium group and n is from 0 to 4.

* * * * *